United States Patent
Shioiri et al.

[11] Patent Number: 6,055,849
[45] Date of Patent: May 2, 2000

[54] GAS DETECTOR AND ITS ADJUSTING METHOD

[75] Inventors: Akira Shioiri, Hyogo; Toshihiro Udaka, Kobe, both of Japan

[73] Assignee: Figaro Engineering Inc., Osaka, Japan

[21] Appl. No.: 09/145,131

[22] Filed: Sep. 1, 1998

[30] Foreign Application Priority Data

Sep. 3, 1997 [JP] Japan ................................. 9-256046

[51] Int. Cl.$^7$ .............................. G01N 7/00; G01N 27/26
[52] U.S. Cl. .......................... 73/31.06; 422/98; 204/417; 73/31.05
[58] Field of Search .............................. 73/31.06, 31.05; 436/151, 152; 204/412, 427; 422/98, 90, 94

[56] References Cited

FOREIGN PATENT DOCUMENTS

| 1-150850 | 6/1989 | Japan . |
| 8-101151 | 4/1996 | Japan . |
| 8-101153 | 4/1996 | Japan . |

OTHER PUBLICATIONS

Analytical Chemistry, vol. 68, No. 13, Jul. 1, 1996, pp. 2067–2072, "Gas Sensing Based on a Nonlinear Respsone: Discrimination between Hydrocarbons and Quantifiation of Individual . . . . . ".

*Primary Examiner*—Hezron Williams
*Attorney, Agent, or Firm*—Nikaido, Marmelstein, Murray & Oram LLP

[57] ABSTRACT

A metal oxide semiconductor gas sensor S is connected to a ladder resistance R, and the output voltage is subjected to logarithmic transformation at plural points on a waveform of temperature change by $$LnR = 2 - 4\, V R1/Vc + LnR1 \tag{1}$$

where R indicating the resistance of the metal oxide semiconductor, V R1 the output voltage to the ladder resistance, Vc the detecting voltage, R1 the resistance of the ladder resistance, and Ln natural logarithm, respectively. Standard signals comprising logarithms of resistance values of the metal oxide semiconductor in plural concentrations and at plural points on the waveform are stored in the EEPROM, and these standard signals and logarithms obtained are compared with each other to detect the gas.

7 Claims, 12 Drawing Sheets

GAS DETECTOR AND ITS ADJUSTING METHOD

FIELD OF THE INVENTION

The present invention relates to detection of a gas with a metal oxide semiconductor gas sensor, and in particular, it relates to a technology of detecting a gas by subjecting a gas sensor to temperature change.

PRIOR ART

An $SnO_2$ type CO sensor TGS203 (TGS203 is a trade name of Figaro Engineering Inc.) is a metal oxide semiconductor gas sensor that uses temperature change. This gas sensor operates in cycles and every cycle has a period of 150 seconds. The first 60 seconds of the cycle are allotted to a higher temperature period, and the subsequent 90 seconds to a lower temperature period. The final temperature of the higher temperature period is 300° C., and the final temperature of the lower temperature period is 80° C. The concentration of CO is detected from the resistance of the metal oxide semiconductor at the end of the lower temperature period. The resistance of the sensor is substantially in inverse proportion to the CO concentration. The ratio of hydrogen sensitivity to CO sensitivity of the sensor is 1:10; for example, hydrogen concentration of 1000 ppm is equivalent to CO concentration of 100 ppm. The initial distribution of the resistance is from 1 to 10 k Ω in CO 100 ppm.

The present inventor worked to improve the overall accuracy of a CO detector using TGS203 and to improve the detection accuracy twice or over by using the same sensor. A problem that the present inventor worked on was the drift of the sensor characteristics. The resistance of TGS203 doubles at the largest in about two months after the start of its service. After that, the resistance decreases to about one half of the initial value at the lowest in several years. As the resistance value of TGS203 is substantially in inverse proportion to the CO concentration, this drift means that the detected value of CO concentration fluctuates within a range of from twice to one half of the actual value. The present inventor worked to reduce the detection error to about ±20% of the true value.

As will be described later, the present inventor found that to correct for the drift, it was effective to correct a signal of the lower temperature range with a signal at the initial period of the higher temperature range. The present inventor also found that concentration dependence of the resistance of TGS203 had variance and that to eliminate errors due to this variance it was necessary to store standard signals relative to plural concentrations.

Hence the gas detector is required to store standard signals of plural points for plural concentrations. This requirement is not compatible with the specification of the conventional CO detector that uses a variable resistor as the load resistance and stores a standard signal as a value of the variable resistor.

Now, the relevant prior art will be described. It has been proposed by Yoshikawa, et al to change the temperature of a gas sensor, regard the behavior of its resistance as a temperature waveform and give the waveform Fourier transform to detect a gas (Analytical Chemistry Vol 68, No. 13, 2067–2072, 1996). It is well known that EEPROM is used as a non-volatile memory in a gas detector. Moreover, it has been disclosed by Okino that when a load resistance is connected to a metal oxide semiconductor gas sensor in series, the output voltage to the load resistance has a linear relationship with the logarithm of the resistance of the metal oxide semiconductor gas sensor (Japanese Patent 2578,624). Okino proposes to keep the ratio of the load resistance to the resistance of the metal oxide semiconductor within an appropriate range by switching the value of the load resistance. Many research works have been reported relative to combination of a signal of a higher temperature range of a gas sensor with that of a lower temperature range thereof (for example, U.S. Pat. No. 4,896,143 and U.S. Pat. No. 4,399,684).

SUMMARY OF THE INVENTION

One object of the present invention is to provide a gas detector using temperature change of a gas sensor with a configuration and an adjusting method that are suited to enhancing the overall accuracy of the gas detector. Other objects will be clear from the description of the actions and effects of the present invention.

According to the present invention, a metal oxide semiconductor gas sensor, of which resistance is changed by gas, is subjected to a temperature change, and signals of plural points of a temperature waveform are used to detect a gas such as CO, ethanol and ammonia. A temperature waveform is the waveform of the sensor signal corresponding to one cycle of the temperature change. In this specification, plural points mean plural points of which times that are measured from the start of the temperature change differ from each other. The kind of the gas sensor is not limited to the $SnO_2$ type. The $In_2O_3$ type, $WO_3$ type, etc. may be used. The target of detection is not limited to CO. Targets include various gases such as ammonia, ethanol and formaldehyde. The temperature change is effected by changing the electric power applied to the heaters of the gas sensor. The pattern of this electric power is called the heater waveform. Various heater waveforms such as square, sine, lamp waveforms can be used.

In the present invention, the gas detector is provided with 1) a non-volatile memory that stores a standard signal that is linear to logarithms of resistance values of a metal oxide semiconductor in combination with plural points on a temperature waveform, 2) a ladder resistance that is connected as a load resistance of a gas sensor; the ratio of its resistance to the resistance of the metal oxide semiconductor is arranged to be within a specified range at plural points, 3) a power source for applying a detecting voltage to a series-connected piece of the ladder resistance and the metal oxide semiconductor, 4) a sampling means for sampling measurement data, that is linear to the logarithm of the resistance value of the metal oxide semiconductor, from the output, that is linear to the output voltage to the ladder resistance, at each of the plural points, and 5) a gas detecting means that compare the combinations of measurement data at plural points with the standard signal to detect a gas.

The combinations of signals at plural points include linear combinations of signals at plural points. For example, plural points are indicated by i=1~n. Signals that are linear to logarithms of resistance values at the respective points are indicated by S1~Sn, and coefficients are indicated by a1~an. Then the linear combination is given by $\Sigma ai \cdot Si$. It is desirable that standard signals are stored for each of plural gas concentrations.

The non-volatile memory may be an EEPROM, a RAM that is built in or attached to a microcomputer and is connected to a back-up battery. The expression linear to"

indicates such a relationship between a signal A and a signal B that they can be mutually expressed by a linear function. For example, the sensor resistance (the resistance of the metal oxide semiconductor) and its logarithm are not linear to each other, but the logarithm of the sensor resistance and the output voltage to the ladder resistance are linear to each other in a narrow range. As will be described later, the greater part of the data processing is expressed by differences between standard signals and measurement data. Addition of constants to measurement data or standard signals has no effects. What is needed is not determining a logarithm of a resistance but determining a quantity that is linear to the logarithm of the resistance. As for the output of the series-connected piece, for example, the output voltage at the junction between the ladder resistance and the metal oxide semiconductor is used. The output, however, is not limited to it. The above-mentioned output voltage may be divided or amplified for use as the output.

The logarithm of the resistance of the metal oxide semiconductor and the output voltage to the ladder resistance are linear to each other within a range that the ratio of resistances of the semiconductor and the ladder is from ½ to 2. Within this range, transformation of the resistance to a logarithm is done by equation (1).

$$LnR = 2 - 4\, VR1/Vc + LnR1 \quad (1)$$

where R indicates the resistance of the metal oxide semiconductor, V R1 the output voltage to the ladder resistance, Vc the detecting voltage, R1 the resistance of the ladder resistance, and Ln natural logarithm, respectively.

As the transformation by equation (1) increases the number of resistors required for the ladder resistance, when the transformation range is to be extended, for example, in terms of R/R1, to a range of from 4 to ¼, nonlinear transformation by equations (2) and (3) is made.

$$LnR = 2x + \tfrac{2}{3} \times x^3 + LnR1 \quad (2)$$

$$x = 1 - 2\, VR1/Vc \quad (3)$$

As will be described later, as the temperature changes, the resistance of the metal oxide semiconductor changes, and to succeed in logarithmic transformation, the ratio of the resistance of the ladder resistance to the resistance of the metal oxide semiconductor needs to be maintained within a proper range. To this end, for example, as the gas concentration does not fluctuate in a single thermal cycle under normal conditions, the resistance values of the metal oxide semiconductor at the respective time points of the preceding thermal cycle may be used to set the resistance value of the ladder resistance in the subsequent cycle. However, if this technique is used, the gas concentration can not be changed quickly in adjusting or testing the gas detector. Hence, preferably, for at least one point of the plural points, the resistance value of the ladder resistance is switched according to the output that is linear to the output voltage to the ladder resistance at the preceding point thereof. The qualification for "at least one point" is given because, for example, when signals of two points are used, if the difference in time between the two points is slight, the resistance value at the subsequent point can be predicted from the resistance value at the preceding point. This technique, however, sets limits to the control of the ladder resistance. Hence, more preferably, the resistance value of the ladder resistance is switched for each of the plural points according to the output at the preceding time point thereof.

As for the non-volatile memory, an EEPROM that requires no back-up battery is desirable. The EEPROM, however, has a limited reliability in the number of access times. RAMs for gas detecting means have limits in capacity in many cases. If the detection range is about ten times as large as the minimum in gas concentration, to suppress the effects of variance of gas concentration dependency, standard signals in, for example, three concentrations are preferable, and the EEPROM is made to store these signals. Usually, the volatile memory such as RAM is made to store standard signals of two lower concentrations, out of the standard signals stored in the EEPROM. If the gas concentration exceeds these two concentrations, the standard signals of a higher concentration will be read out from the EEPROM and written into the volatile memory, and if the gas concentration drops, the standard signals of the two lower concentrations will be stored in the volatile memory. With this arrangement, the number of times of access to the EEPROM can be reduced to prevent troubles.

The present invention is characterized in that 1) a non-volatile memory that stores a standard signal that consists of Fourier transformation components of logarithms of resistance values of a metal oxide semiconductor in plural gas concentrations, 2) a ladder resistance that is connected as a load resistance of a gas sensor; the ratio of its resistance to the resistance of the metal oxide semiconductor is arranged to be within a specified range, and preferably, within a specified range usually, 3) a power source for applying a detecting voltage to a series-connected piece of said ladder resistance and said metal oxide semiconductor, 4) a sampling means for transforming the output that is linear to the output voltage to the ladder resistance and, at multiple points on the waveform, sampling measurement data, that is linear to the logarithm of the resistance value of the metal oxide semiconductor, and 5) a gas detecting means that gives Fourier transformation to said multiple pieces of measurement data and compares them with the standard signal to detect a gas are provided. For better quantification of gas concentrations, preferably, standard signals at plural gas concentrations are stored and composed.

The Fourier transformation signals indicate characteristics of the temperature waveform of the gas sensor, and directly processing the logarithm of the sensor resistance is practically identical to processing the logarithm of the sensor resistance after Fourier transformation. Hence the description concerning directly processing the logarithm of the sensor resistance in this specification also applies to the case of using Fourier transformation.

The present invention is an adjusting method of an apparatus for changing the temperature of a metal oxide semiconductor gas sensor, of which resistance is changed by a gas, and detecting the gas, characterized in that a: is provided a non-volatile memory that stores a standard signal that is linear to logarithms of resistance values of the metal oxide semiconductor as a combination of plural points on the waveforms of the resistance values of the gas sensor being subjected to a temperature change, and b: the gas sensor is exposed to a gas of a specified concentration and subjected to the temperature change, signals linear to the logarithms of the resistance values of the metal oxide semiconductor are obtained at plural points to generate said standard signals, and they are stored in said non-volatile memory as the standard signal.

Preferably, the step b is repeated for plural gas concentrations.

The invention will be described. To improve the overall accuracy of a gas detector, it is necessary to use a standard signal at plural points. Hence the signal is stored in a non-volatile memory. As will be indicated in an embodiment, logarithms of resistance values of the metal oxide semiconductor rather than the resistance values thereof are easier to handle as the standard signal. In other words, if resistance values of the metal oxide semiconductor are directly used, calculations for compensation through combination of signals will become more complex, and a small-sized microcomputer will not be able to process them. Hence, in the present invention, signals linear to logarithms of the resistance values of the sensor rather than the resistance values of the sensor are used.

As the temperature changes, the sensor resistance will change significantly. It is necessary to transform a wide range of resistance values into logarithms with ease. As the transformation range of the sensor resistance is wide, a ladder resistance is used to maintain the ratio of the resistance thereof to the resistance of the metal oxide semiconductor within a specified range at required points. Here the required points are, for example, points on the temperature waveforms used for the standard signal. Now, when the resistance of the ladder resistance and the resistance of the metal oxide semiconductor are within specified ranges, the output voltage to the ladder resistance or a signal linear to that is in a linear relationship with the logarithm of the sensor resistance. Hence if the ladder resistance is connected to the metal oxide semiconductor, the value of the load resistance is kept in a specified range, and the output voltage to the load resistance or the like is used, a measurement data, that is linear to the logarithm of the sensor resistance within a range that can be processed by a small-sized microcomputer, can be obtained. When measurement data is obtained in the above-mentioned manner, it is compared with the standard signals to detect the gas.

The logarithm of the sensor resistance is expanded in series with the output voltage to the load resistance, and terms of up to the first degree are considered. Then equation (1) is obtained $$LnR = 2 - 4\ VR1/Vc + LnR1 \quad (1)$$

As is clear from this, the logarithm of the sensor resistance is linear to the output voltage $VR1$, and the logarithm of the sensor resistance can be obtained within the range of linear transformation.

The range of transformation is narrow for the logarithmic transformation by equation (1), and the range of the ratio of the sensor resistance $R$ to the resistance of the load resistance $R1$ is limited to from about 2 to ½. Within this range, the transformation error is ±2% or under. To widen the range of transformation, the logarithm of the sensor resistance is expanded into series up to the third degree, and the logarithmic transformation by equations (2), (3) is made. With this, when the value of $R/R1$ is from 4 to ¼, the transformation error is 4% or under.

To obtain the logarithm of the sensor resistance, it is necessary to keep the resistance of the ladder resistance properly. Hence, for at least one point of plural points for sampling measurement data, the resistance of the ladder resistance is switched according to the output at the preceding point thereof. In this way, even when the gas concentration is changed rapidly during adjustment or test of a gas detector, the value of the load resistance (the resistance of the ladder resistance) can be maintained properly.

As for the non-volatile memory, an EEPROM that requires no back-up battery is desirable. As for standard signals, it is desirable to store signals at at least three concentrations. Usually the capacity of a RAM of a microcomputer used for a gas detector is small, standard signals at two concentrations are normally sent from the EEPROM into the RAM. If the gas concentration exceeds the concentration of the standard signals, standard signals of a higher concentration will be sent from the EEPROM into the RAM. If the gas concentration drops, standard signals of the lower concentration will be stored in the RAM again. The number of times of access to the EEPROM is limited. For example, about 100,000 times of access is considered to be the upper limit for assuring the reliability. If one cycle of temperature change is, for example, one minute, and the EEPROM is accessed every time, the reliability of the EEPROM will be lost in about 70 days. However, under normal conditions, it is rare that the gas concentration exceeds the two concentrations of the lower concentration side, and the access to the EEPROM is limited to this case and when the gas detector is reset. Normally such occasions are not frequent, and with the limited access of 100,000 times, the reliability of the EEPROM can be maintained.

Detecting a gas by using plural points on a temperature waveform is equivalent to, for example, detecting a gas by determining the characteristic function of the temperature waveform through Fourier transformation. Hence gas detection by directly using the logarithm of the sensor resistance can be replaced by gas detection through Fourier transformation of the logarithm of the sensor resistance. In this case, as for the Fourier transformation, the sine component and the cosine component of the fundamental wave components of which frequency is equal to that of the temperature change of the sensor, or the harmonics thereof may be used. It is not necessary to use all the Fourier transformation components from the zero degree to the infinite degree. In an extreme case, one component may be used. The sine component and the cosine component are regarded as different components from each other. Preferably, two to six components are used.

Next, to adjust such a gas detector, it is necessary to store standard signals in the non-volatile memory. Hence the non-volatile memory is enabled during adjustment. The gas sensor is subjected to temperature change, and in the specified concentration of the gas, signals at specified timing points or a linear sum of these signals are written in the non-volatile memory. Preferably, this processing is repeated by changing the gas concentration to store the standard signals at the required number of gas concentrations in the non-volatile memory. This processing can be made by setting the gas detector in an adjusting chamber, or by setting the sensor only in the adjusting chamber, processing the signals thereof in a personal computer, etc. and writing them into the non-volatile memory. When a personal computer, etc. is used, there is no limit of processing capability. Hence the sensor resistance may be directly AD-converted and subjected to logarithmic transformation, and the result may be used as a standard signal.

In the present invention, signals that are required for compensating signals of gas sensor can be easily stored in a non-volatile memory. Standard signals are not obtained by adjusting a variable resistance. They are obtained by storing in a non-volatile memory. Hence there is no need of adjusting the variable resistance whenever an adjustment is made. If standard signals are stored for plural gas concentrations, errors due to variance of the gas concentration dependence will be reduced. As the output to the ladder resistance is used to make logarithmic transformation, even a small-sized microcomputer can easily obtain measurement data that is linear to the logarithm of the sensor resistance.

EMBODIMENT

Figure 1:
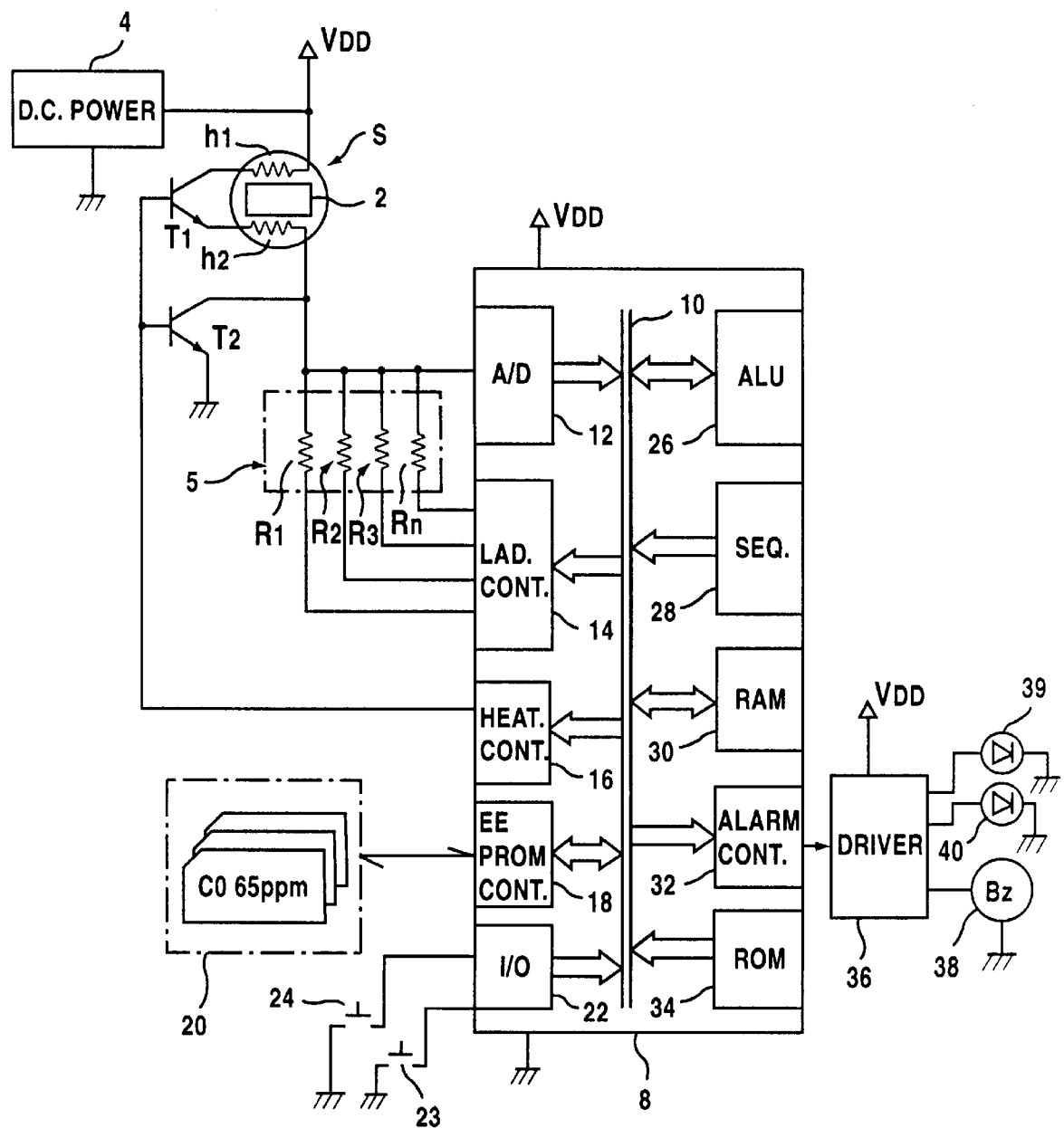
FIG. 1 is a block diagram of a gas detector of an embodiment.

An embodiment and a modification thereof are shown in FIG. 1 through FIG. 14. The configuration of the embodiment is shown in FIG. 1. S denotes a metal oxide semiconductor gas sensor. Here TGS203 is used. It is an $SnO_2$ type metal oxide semiconductor 2 with a pair of heaters h1, h2 arranged at both ends thereof. The kind and configuration of the sensor S are arbitrary. 4 denotes a direct-current power source such as 5 V DC. Its output V DD is used to drive the gas detector. To drive the pair of heaters h1, h2 of the gas sensor S jointly, transistors T1, T2 are used; these transistors are turned on/off concurrently. When both the transistors T1, T2 are turned on, currents will flow through the heaters h1, h2. The temperature of the metal oxide semiconductor 2 is changed periodically by changing the duty ratio of on of the transistors T1, T2. Here, according to the operating conditions of TGS203, a higher temperature range is set for 60 seconds and a lower temperature range is set for 90 seconds. The waveform of the heater electric power is a rectangular waveform that changes between of the higher temperature range and the lower temperature range. The final temperature of the higher temperature range is 300° C., and the final temperature of the lower temperature range is 80° C. In the embodiment, the time is expressed as follows: The 0th second is set at a point immediately before the completion of the lower temperature period. The period of from the 0th second to the 60th second is the higher temperature period, and the period of from the 60th second to the 150th second (the 150th second is also the 0th second) is the lower temperature period.

A ladder resistance 5 is connected to the metal oxide semiconductor 2, and R1 through Rn denote individual resistors thereof. Here, every resistor of R1 through Rn has a resistance that is four times as large as that of the immediately preceding resistor. For instance, are used six resistors; 0.5 k Ω, 2 k Ω, 8 k Ω, 32 k Ω, 128 k Ω and 512 k Ω. It is easy to obtain fixed resistors having an accuracy of about ±2%. Thus AD conversion error due to switchover of resistors is about ±2%. When the transistors T1, T2 are turned off, the power output V DD (hereinafter called the detecting voltage Vc) will flow, via the metal oxide semiconductor 2, to the ladder resistance 5. The output voltage to the ladder resistance 5 is AD-converted.

8 denotes a microcomputer. Here, a 4-bit one-chip microcomputer is assumed. 10 is the bus thereof. 12 is, for example, an 8-bit AD converter. 14 is a ladder resistance control. Only one resistor of the resistors R1 through Rn is earthed, and this earthed resistor is used as the load resistance. As described above, the output voltage to the ladder resistance is AD-converted by the AD converter 12. It is a matter of course that the output voltage to the ladder resistance 5 may be divided before AD conversion. Moreover, the voltage on the sensor S side, rather than the voltage on the resistor ladder 5 side, may be AD-converted. 16 denotes a heater control that controls turning on/off of the transistors T1, T2 to generate the higher temperature range of 60 seconds and the lower temperature range of 90 seconds. 18 denotes an EEPROM control, and 20 denotes an EEPROM.

Figure 3:
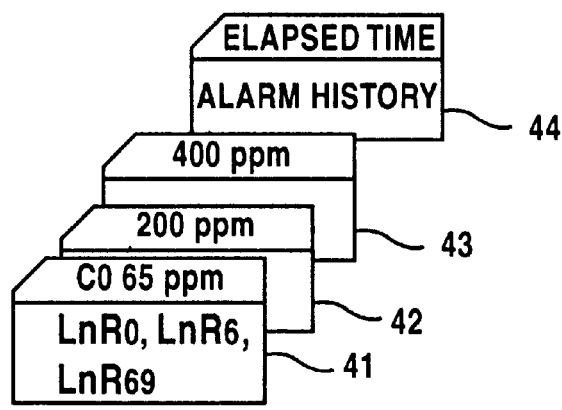
FIG. 3 is a diagram showing the configuration of an EEPROM of the gas detector of the embodiment.

The configuration of the EEPROM 20 is shown in FIG. 3. Here it is assumed that, for example, the detection target is CO and the detection range is from CO 50 ppm through 600 ppm; the maximum is about ten times as large as the minimum. Reference signal sets are of three points; CO 65 ppm, 200 ppm and 400 ppm. Each set of standard signals comprises the logarithm of the sensor resistance at 0th second LnR0, the logarithm of the sensor resistance at the 6th second LnR6, and the logarithm of the sensor resistance at 69th second (the early part of the lower temperature period) LnR69. Ln denotes natural logarithm, and the subscript, such as 0 of R0, indicates the timing point measured from the 0 second. Similarly, three standard signals, logarithms of the sensor resistance values at the 0th second, the 6th second and the 69th second are stored for CO 200 ppm and CO 400 ppm, respectively. 41 through 43 denote cards. A set of standard signals for one concentration level are considered as a card. In addition to them, there is a card 44 on which are kept records of use of the CO detector. In other words, the total time of use and the past CO alarm records are stored on the card 44. The total time of use is the cumulative time when the power source of the CO detector was on. For example, the unit of time may be a day, and the cumulative time of use is stored in the card 44. As for records of alarm, whenever a buzzer, that will be described later, is made to buzz, the date will be recorded. As for this date, the same standard as the total time of use is used to record the date. With this arrangement, the date when the buzzer is activated can be identified.

22 denotes an input/output unit to which an adjusting switch 23 and a reset switch 34 are connected. When the adjusting switch 23 is turned on, the EEPROM control 18 will be able to write in EEPROM 20. This switch is used only when the CO detector is adjusted. The reset switch 24 is one for stopping the buzzer 38.

Figure 2:
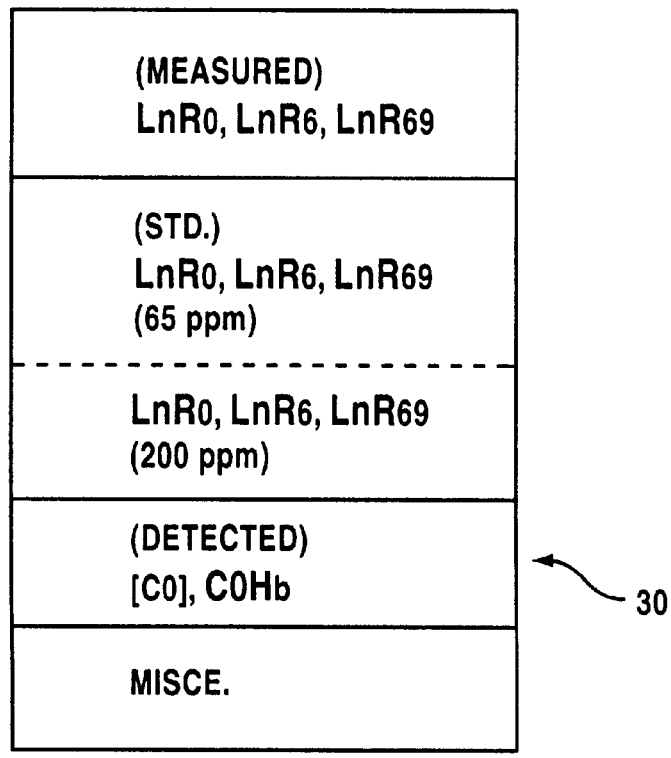
FIG. 2 is a diagram showing the configuration of a RAM of the gas detector of the embodiment.

The microcomputer 8 has a 4-bit arithmetic and logic unit 26. It also has a sequence control 28 for operating the CO detector at a cycle of 150 seconds. The sequence control 28 has a built-in timer. 30 denotes a RAM that is used as a volatile memory, and its configuration is shown in FIG. 2. In the RAM 30, are stored standard signals of two sets of three pieces of measurement data, LnR0, LnR6 and LnR69 for two concentrations. Normally are used standard signals for lower concentrations, 65 ppm and 200 ppm. When the gas concentration exceeds 200 ppm, the standard signals for 65 ppm will be replaced with those for 400 ppm. When the gas concentration drops to 200 ppm or under, the standard signals for 400 ppm will be replaced with those for 65 ppm. The gas detection range is from 50 to 600 ppm, and the range of from 50 to 65 ppm is close to the standard signal of 65 ppm. The range of from 400 to 600 ppm is 1.5 times as large as 400 ppm of the standard signals, and the gas concentration can be determined accurately by using the standard signals for 400 ppm. For the remaining range, when CO is generated, the gas concentration can be determined by using the standard signals for concentrations that are on both sides of the actual CO concentration to make interpolation between the two standard signals.

In the RAM 30, in addition to the above-mentioned data and signals, are stored a CO concentration determined, COHb (carbon monoxide hemoglobin concentration in blood) reduced from the CO concentration, and other auxiliary signals (for example, time data for constituting a timer of which unit is a day).

With reference to FIG. 1 again, 32 denotes an alarm control that actuates, via a drive circuit 36, LED 39 and LED 40. When the CO hemoglobin concentration in blood exceeds, for example, 5%, the alarm control 32 will actuate the buzzer 38. When the buzzer 38 is turned on, the EEPROM control 18 will write the date of the alarm in the card 44. 34 denotes a program memory in which data such as various constants for temperature compensation are stored. These data are fixed data common to the sensor S and other sensors. All the data for individual sensors are stored in the EEPROM 20.

Figure 4:
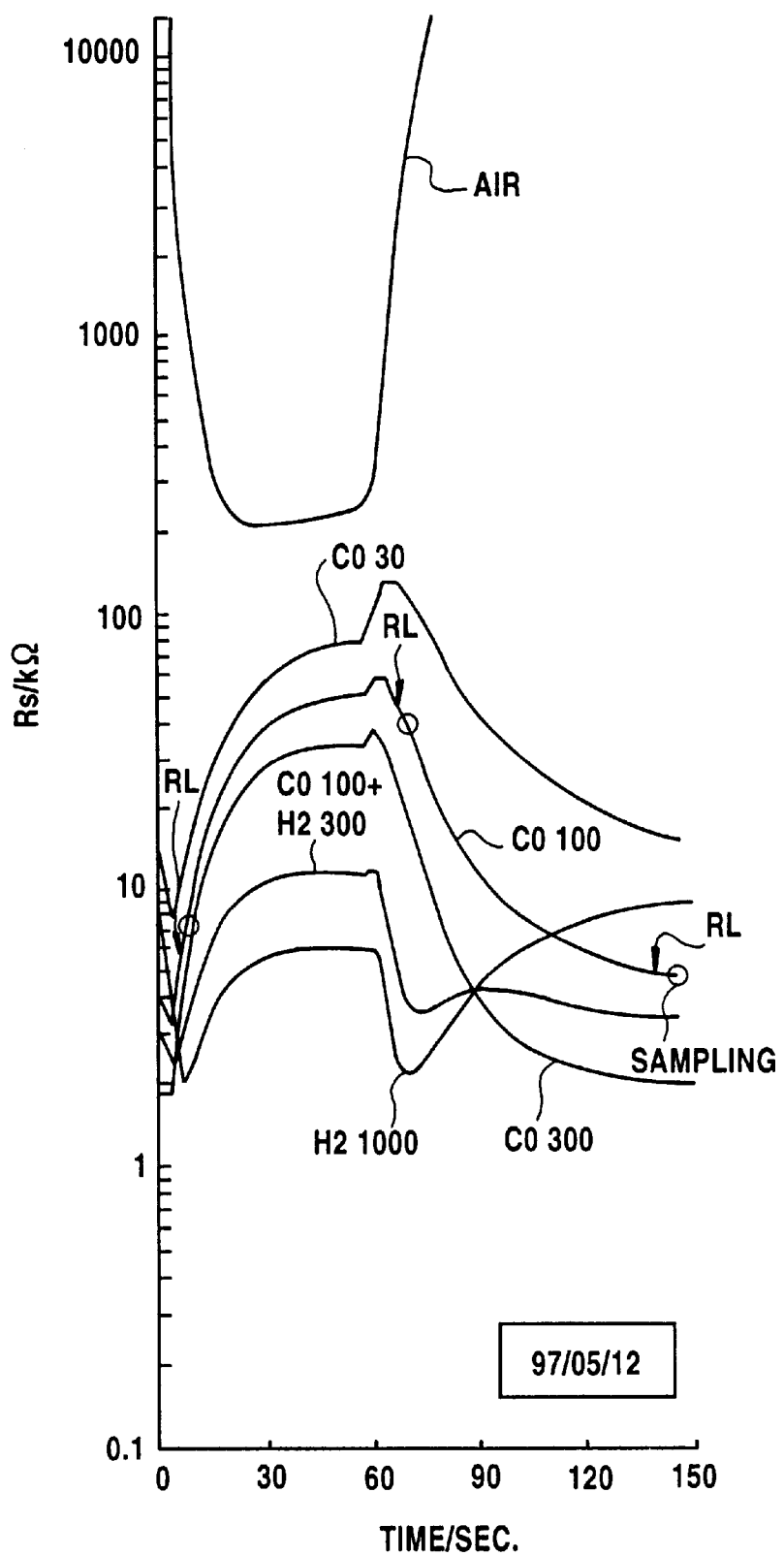
FIG. 4 is a characteristic diagram showing the waveform of the resistance of a gas sensor used in the embodiment.

Mean temperature waveforms of ten sensors are shown in FIG. 4. Sampling points, that are used in the embodiment, are marked by ○ on the waveform of CO 100 ppm; sampling is made at the 150th second, the 6th second and the 69th second. The sensor resistance changes by about ten times in the range of from CO 30 ppm to 300 ppm. The resistance at the 0th second and that at the 69th second differ from each other by a factor of about 10. When the dispersion in the sensor resistance, fluctuations in ambient temperature, etc. are added to them, the range of AD conversion is, in resistance, from about 0.5 to 500 k Ω. To achieve AD conversion in this range, the resistances R1 through Rn are changed in six steps, ranging from 0.5 k Ω to 512 k Ω, any resistance being four times greater than the immediately preceding one. Immediately before each sampling time, the output VR1 to the ladder resistance is monitored, and the load resistance is changed according to the output VR1. AD conversion of VR1 can be done within 1 second, On the basis of the value at the time, use of which resistance at each sampling point can be determined.

Figure 5:
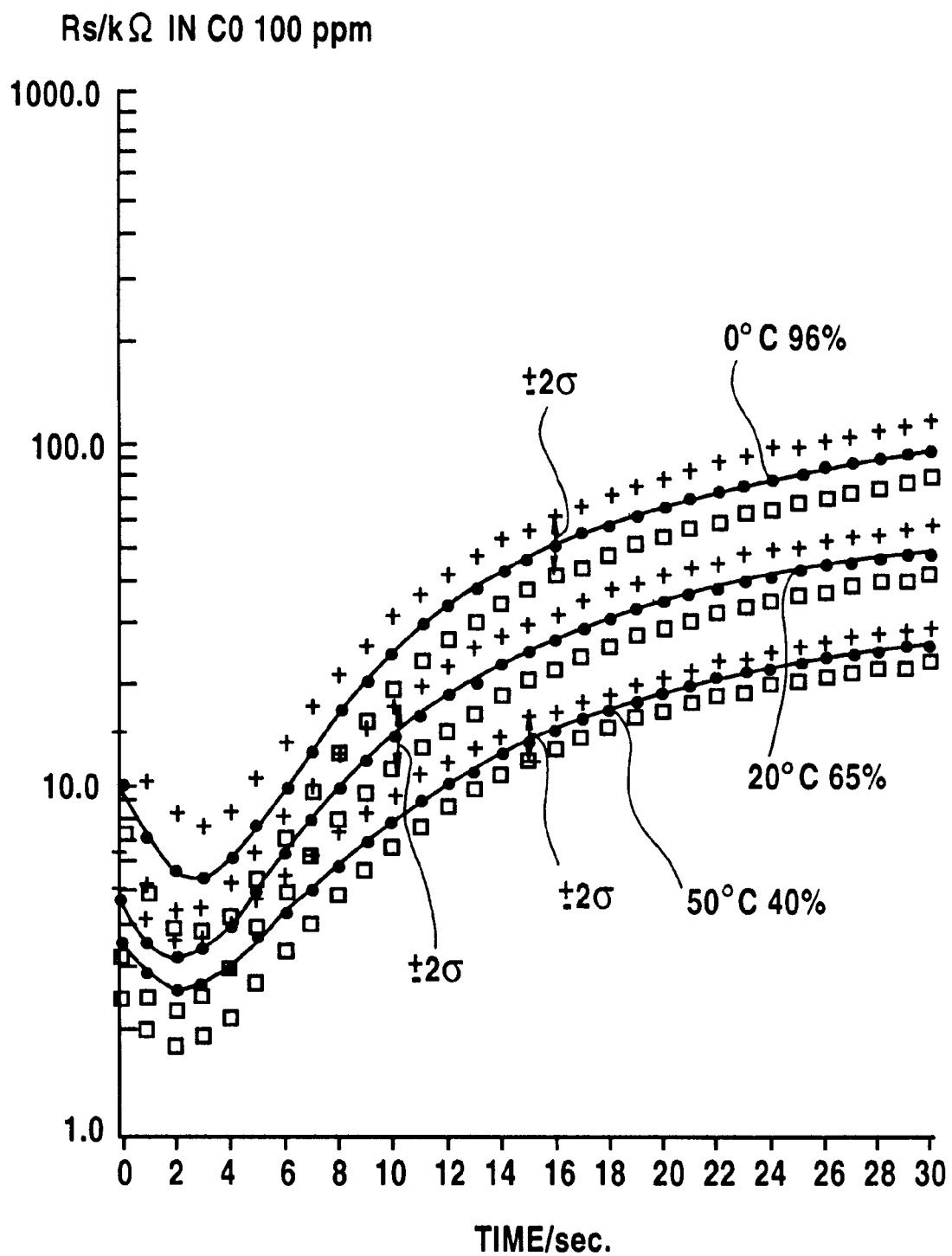
FIG. 5 is a characteristic diagram showing the resistance waveform in the early part of the higher temperature range of the gas sensor used in the embodiment.

FIG. 5 shows enlarged temperature waveforms of other ten sensors in the early part of the higher temperature range. The atmospheres are of three kinds; 0° C. and relative humidity of 96%, 20° C. and 65%, and 50° C. and 40%. The range of ±2 δ (δ is the standard deviation) and the mean value are shown for each waveform. The gas concentration is CO 100 ppm. The resistance at each timing point varies by a factor of a little under 10 due to changes in ambient temperature and humidity. The resistance at the 0th second and the resistance at the 6th second are substantially identical to each other. Hence, for example, the same load resistance as that at the 0th second may be used for the 6th second. However, preferably, the resistance at the 0th second is determined from, for example, the signal at the 148th second (or at the 149th second to make more reliable sampling before the transition to the higher temperature range), and the load resistance at the 6th second is determined from the resistance at the 5th second. Similarly, the load resistance at the 69th second is determined from the resistance at the 68th second.

Figure 6:
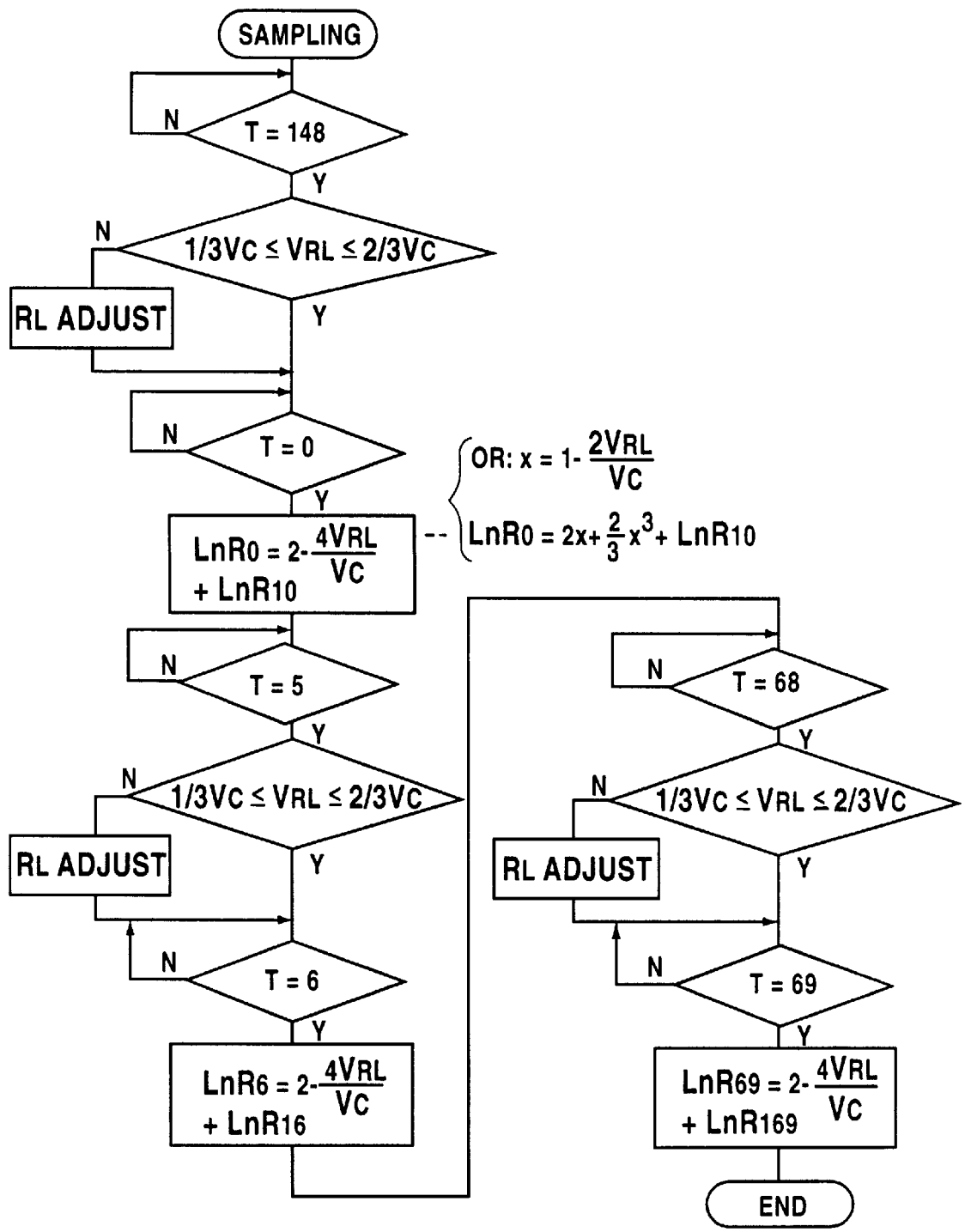
FIG. 6 is a flow chart showing the sampling algorithm of the gas detector of the embodiment.

FIG. 6 shows the algorithm of the sampling. When the time reaches the 148th second, the output voltage will be AD-converted, and this value will be checked whether it is within a range of from $1/3$ to $2/3$ of the detecting voltage Vc (identical to V DD). When the value is within this range, the ratio of the sensor resistance to the load resistance is within a range of from 2:1 to 1:2. If the output voltage is adequate, the same load resistance will be used. If the output voltage is not adequate, the load resistance will be changed to bring the output voltage within the above-mentioned range. Next, when the time reaches the 0th second, the output voltage will be AD-converted, and the AD-converted output voltage V R1 will be used to determine the logarithm of the sensor resistance at the 0th second by equation (1). Similarly, at the 5th second, the value of the load resistance is checked whether it is correct or not. Then the logarithm of the sensor resistance at the 6th second will be determined. Further, at the 68th second, the value of the load resistance is checked whether it is correct or not, and at the 69th second, the logarithm of the sensor resistance is determined.

$$\text{Ln}R = 2 - 4VR1/Vc + \text{Ln}R1 \tag{1}$$

If the logarithm of the sensor resistance is approximated up to the term of the first degree, as shown in equation (1), when R/R1 is 1, the error is 0, when R/R1 is $1/2$ or 2, the error is 2%, and when R/R1 is $1/3$ or 3, the error is 11%. In the embodiment, as it is aimed to detect the CO concentration with an error of ±20% or under, the error of ±10% is too large. Hence the ladder resistance 5 is controlled so that the ratio of the sensor resistance to the load resistance is within a range of from 2 to $1/2$ at three points of the 0th second, the 6th second and the 69th second.

The transformation of VR1 to the logarithm of the sensor resistance by equation (1) is a linear transformation and is a very simple transformation. However, this requires six load resistors. To reduce the number of load resistors required, for example, to four, it is necessary to keep R/R1 within a range of from 4 to $1/4$, or more preferably, within a range of from $\sqrt{8}$ to $1/\sqrt{8}$. For this, it is necessary to make transformation up to the term of third degree. When the logarithm of the sensor resistance is expanded into series with VR1, there will be no term of the second degree. We will have equations (2), (3) in which terms up to the third degree are considered. If equations (2), (3) are used, when R/R1 is 1, the transformation error is 0%, when R/R1 is $1/4$ or 4, the transformation error is 4%, and when R/R1 is $1/3$ or 3, the transformation error is 2%. Hence in resistors R1 through Rn, the resistance of the subsequent resistor is increased by 16 times, or preferably by 8 times or 9 times. For example, the resistance R1~Rn comprise 4 kinds, 1 k Ω, 8 k Ω, 64 k Ω and 512 k Ω. With this arrangement, a range of from 0.5 to 1 M Ω can be transformed into logarithm with an error of 2% or under.

$$\text{Ln}R = 2x + 2/3 \times x^3 + \text{Ln}R1 \tag{2}$$

$$x = 1 - 2\ VR1/Vc \tag{3}$$

Figure 7:
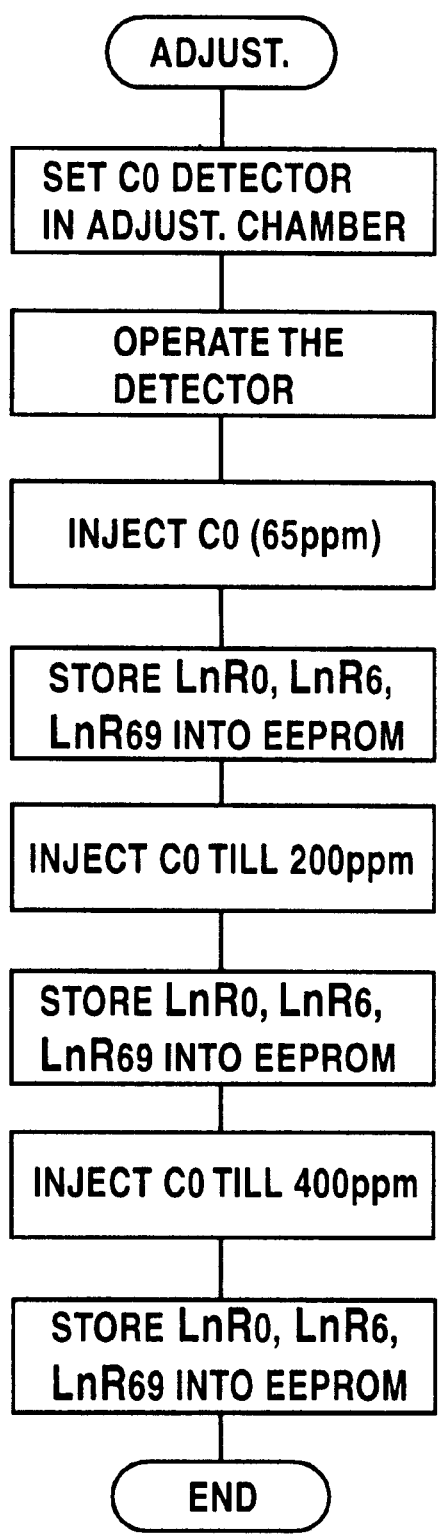
FIG. 7 is a flow chart showing the adjustment algorithm of the gas detector of the embodiment.

The procedure for adjusting the gas detector of FIG. 1 is shown in FIG. 7. At the time, the adjusting switch 23 is turned on so that standard signals can be written into the EEPROM 20. The procedure will be described by assuming that the CO detector is set in an adjusting chamber. After the CO detector is set, the power source is turned on to operate the detector. Next, CO is injected, for example, up to 65 ppm. Then the microcomputer 8 generates LnR0, LnR6 and LnR69 to write them into the RAM 30. They are written in the card 41 of the EEPROM 20. Next, the CO concentration is increased to 200 ppm, and similar steps are repeated. Then the CO concentration is increased to 400 ppm. In this way, by increasing the CO concentration with the specified steps, standard signals can be written into the EEPROM 20. Thus there is no need of adjusting a variable resistor to store a standard signal. The adjusting work can be done with ease.

It is assumed here that the CO detector is set in an adjusting chamber. However, only a sensor S may be set in an adjusting chamber. Then, the resistance of the sensor S is AD-converted by an AD converter of, for example, 12 bit, and it is stored in a personal computer or the like, and in turn, it is written into the EEPROM 20. In this case, the sensor S is not assembled into the CO detector, and the sensor S and the EEPROM are treated as a set. They are connected with a CO detector that is assembled separately. The portion of the CO detector other than the sensor S and the EEPROM 20 can be handled in the same manner as conventional electronic circuits, and even a manufacturer with no experience on gas sensors can assemble a CO detector.

Figure 8:
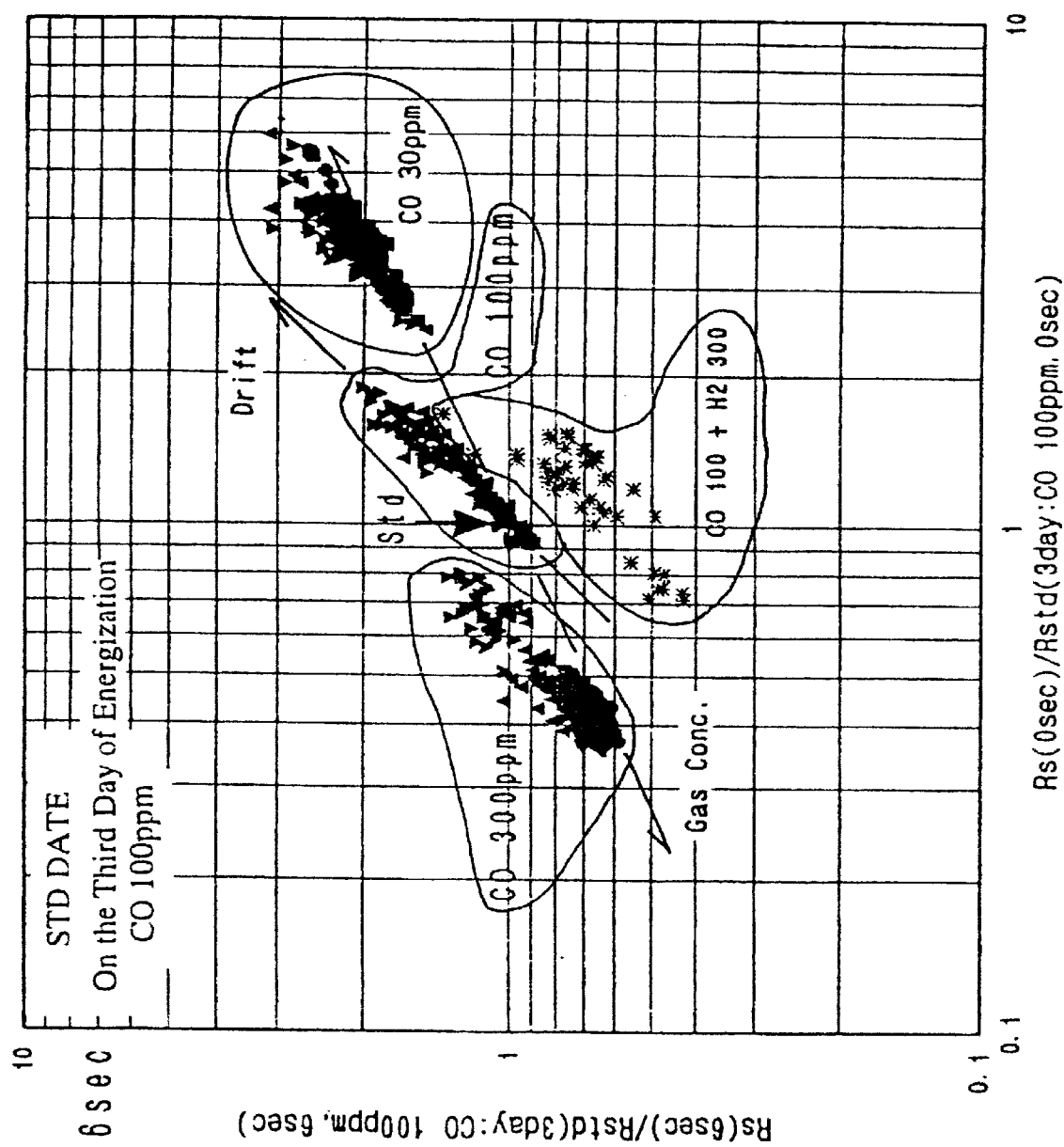
FIG. 8 is a characteristic diagram showing the variation of characteristics due to drift of the gas sensor used in the embodiment.

The drift compensation of the gas sensors is shown in FIG. 8. The data was taken from 45 samples of TGS203. These samples included defective samples (7 samples), non-defective samples (20 samples), samples that were left to stand for two years (8 samples), and samples that were set on CO detectors and recovered eventually (10 samples). The axis of abscissa of the diagram shows the sensor resistance at the 0th second on a logarithmic scale, and the axis of ordinate shows the sensor resistance at the 6th second on the logarithmic scale. 1 on the axis of abscissa indicates the standard signal at the 0th second in CO 100 ppm (on the third day after the start of energization), and 1 on the axis of ordinate indicates the standard signal at the 6th second in CO 100 ppm (on the third day after the start of energization). Data in FIG. 8 is normalized by standard signals that were generated in CO 100 ppm on the third day of energization. The respective points on the diagram show the measuring points in the course of five weeks of energization. When 45 samples of TGS203 were used for five weeks, some samples increased in resistance and some others decreased in resistance accidentally. These points, however, concentrate on a narrow straight line having a gradient of 1 on a two-dimensional plane of the 6th second resistance and the 0th second resistance. This axis is called a drift axis. Drift axes are not distinct for the data taken in CO 30 ppm and 300 ppm. This is due to variance of the concentration dependence of TGS203. As their concentration dependence is not homogeneous, the initial points in CO 30 ppm and 300 ppm do not coincide at one point. Because of variance of the initial points, their drift axes are indistinct. A straight line connecting three points of CO 30 ppm, 100 ppm and 300 ppm is called the CO concentration axis. Data points corresponding to the initial characteristics of the samples of TGS203 are on this concentration axis. With the use, the concentration axis translates parallel in the direction of the drift axis.

Figure 9:
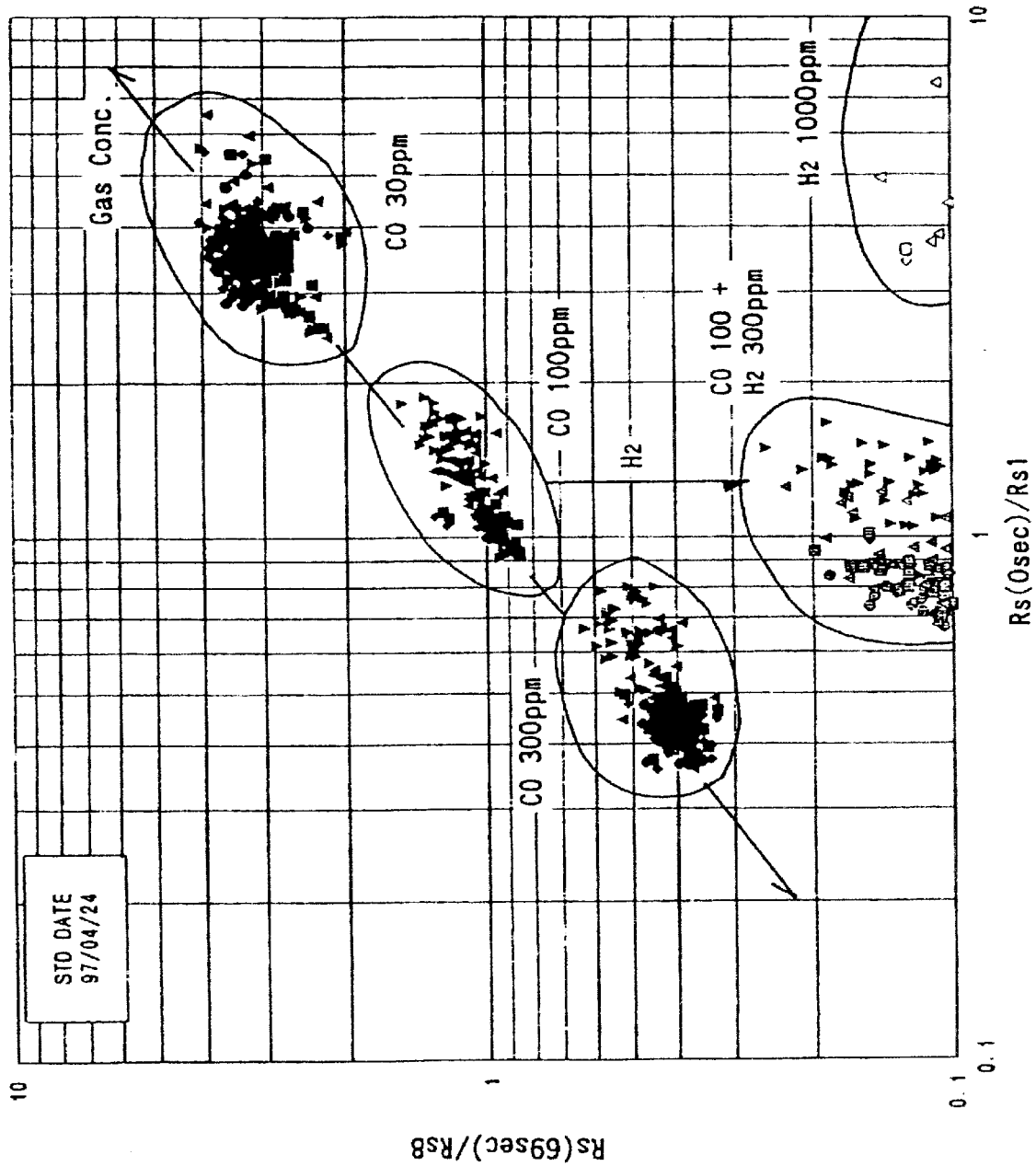
FIG. 9 is a characteristic diagram showing detection of hydrogen with the gas sensor used in the embodiment.

In addition to the above-mentioned data, the behavior of a mixed gas of CO 100 ppm and hydrogen 300 ppm is indicated in FIG. 8. The behavior in hydrogen 1000 ppm is also indicated. As for these behaviors, the points for the energization period of five weeks are indicated by sensor. As can be clearly seen in FIG. 8, the sensitivity to hydrogen is slightly negative. For example, let us translate the respective points of CO 100 ppm+hydrogen 300 ppm parallel to the drift axis. Then we get intersection points of these points with the CO concentration axis. The resulting concentration range is from CO 80 ppm to 60 ppm. On the other hand, the distribution of points in CO 100 ppm for five weeks is narrow. When these points are translated parallel to the drift axis, the resulting intersection points with the CO concentration axis give a distribution range of from CO 80 ppm to 120 ppm. The sensitivity to hydrogen becomes negative because the hydrogen sensitivity of the 6th second signal is higher than that of the 0th second signal. To correct this, a combination of the 0th second signal and the 69th second signal is used. Energization data for five weeks of this case are shown in FIG. 9. As can be clearly seen in FIG. 9, when hydrogen is present, the resistance at the 69th second decreases significantly. Thus data points are extremely away from the CO concentration axis. Hence the distance of descent from the CO concentration axis towards the bottom of FIG. 9 is used as a hydrogen concentration signal.

The hydrogen concentration signal is not an accurate one. However, the hydrogen sensitivity is small, and the signal is for its compensation. Thus we can use a hydrogen detection signal that lacks quantitativeness. In correcting the hydrogen sensitivity, two approaches may be taken. One is to restore the hydrogen sensitivity to zero, that is slightly negative in FIG. 8; in other words, to design a CO detector that is extremely selective and sensitive to CO only. Another approach is to make compensation so that the CO detector's ratio of CO sensitivity to hydrogen sensitivity is 10:1, just like the intrinsic characteristic of TGS203. Choice between these two approaches is an issue of design approach of the CO detector.

Figure 10:
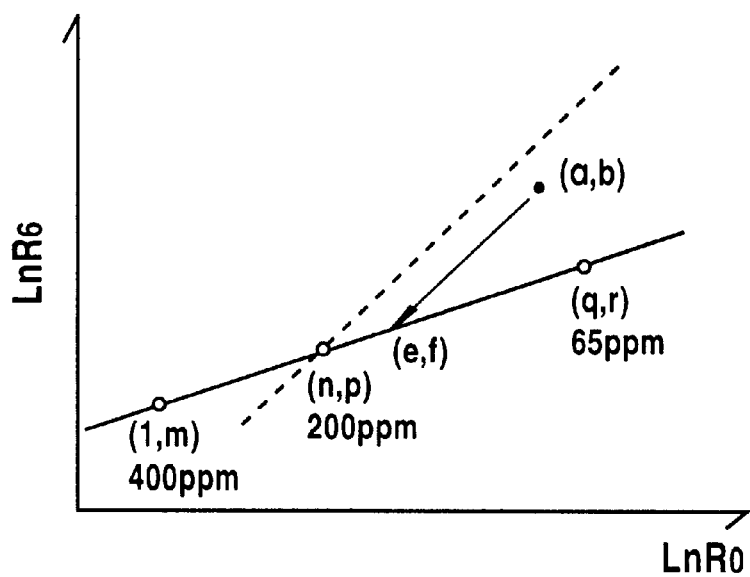
FIG. 10 is a characteristic diagram showing a mechanism for computing CO concentration in the embodiment.

The principle of drift compensation is shown in FIG. 10. The solid line in the diagram is the CO concentration axis, and the dashed line is the drift axis. The standard signals at three points in 65 ppm, 200 ppm and 400 ppm are stored in the EEPROM 20. A point (a, b) in a topological space of two dimensions LnR0 and LnR6 is determined by measurement. The coordinates of the respective standard signals in this topological space are defined as shown in FIG. 10. The point (a, b) is translated parallel to the drift shaft, and its intersection point with the CO concentration axis is defined to have coordinates (e, f).

Figure 12:
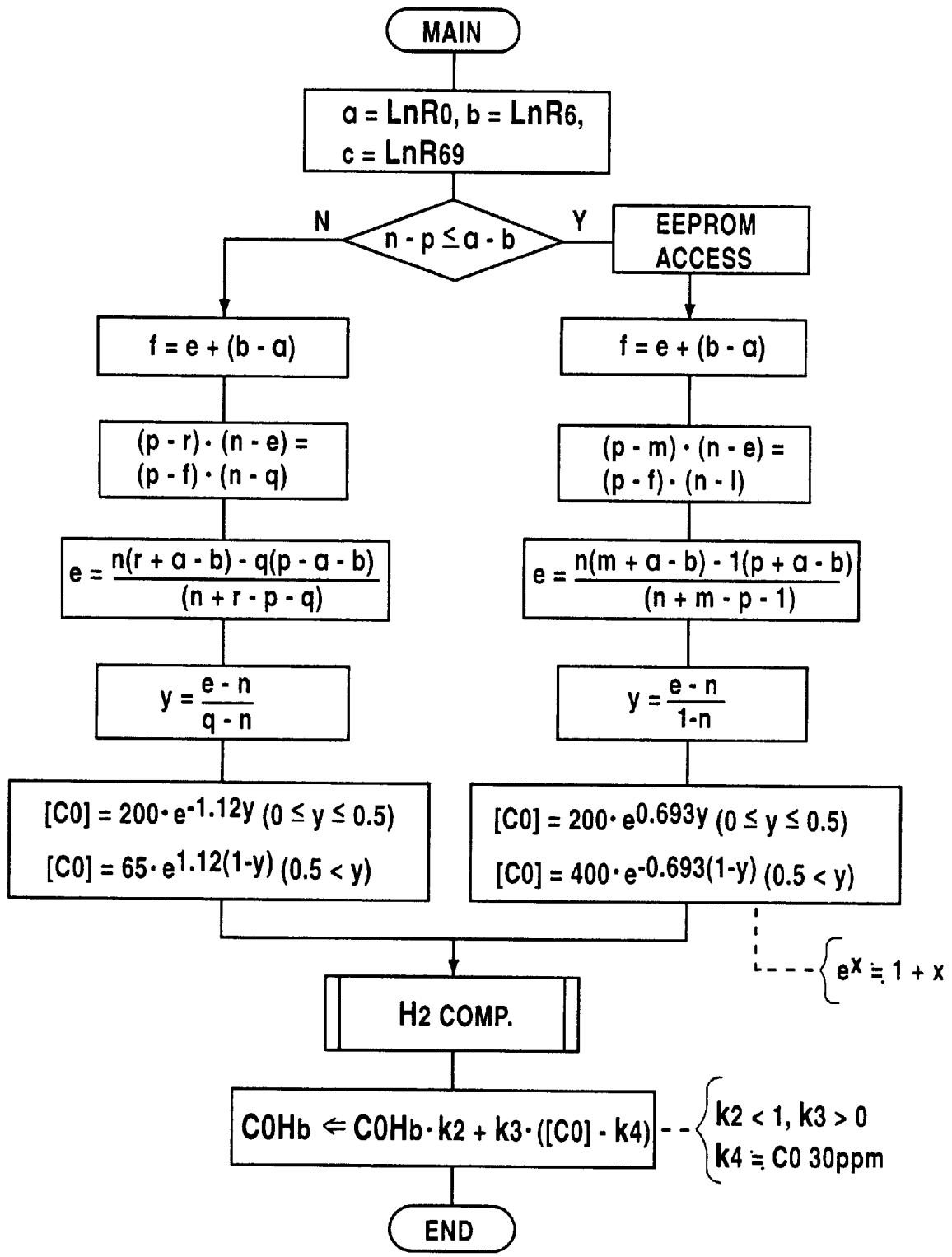
FIG. 12 is a flow chart showing the main loop of the gas detector of the embodiment.

Calculation of CO concentration using FIG. 10 is shown by the main loop of FIG. 12. Three variables, a, b and c are defined by measurement data. Next, in FIG. 10, a check is made whether (n−p) is equal to or greater than (a−b). If this condition is not met, when the drift axis is extended from the point of 200 ppm, the measurement point is below the drift axis, and the detected concentration is 200 ppm or under. The gradient of the drift axis is 1, and (e−a) equals (f−b). Then we get f=e+(b−a). Next, the point (e, f) divides internally the segment that is defined by two standard signals of 65 ppm and 200 ppm. Hence e and f and the coordinates n, p, q, r of the standard signals of 65 ppm and 200 ppm are constrained by a single relation. Thus the coordinate e can be determined by using this relation. It should be noted that what are actually handles here are variable such as (n−e), (p−f) and (e−f). They correspond to differences in logarithms, and actually, they directly correspond to differences in VR1. Hence it is obvious that it is sufficient to determine VR1 without making the above-mentioned logarithmic transform nor seeking the logarithms of sensor resistances.

When the value e is determined, the next step is to determine the internal ratio y of the segment between 65 ppm and 200 ppm. When y is 0, the CO concentration is 200 ppm. When y is 1, the CO concentration is 65 ppm. The concentration varies along the segment in a range about three times as large as the minimum. If this is solved directly, the series expansion of exp(y) will require terms of the second degree or over. Hence we assume a midpoint between 65 ppm and 200 ppm. For any point towards 200 ppm of the midpoint, series expansion is based on the concentration of 200 ppm. For any point towards 65 ppm of the midpoint, series expansion is based on the concentration of 65 ppm. With this arrangement, approximation by exp (y)=1+y hardly generates approximation errors. In this way, the CO concentration before hydrogen concentration compensation is determined.

Now, when the obtained topological point is above the drift axis that passes CO 200 ppm, the CO concentration exceeds 200 ppm. In this case, the EEPROM 20 is accessed, and the standard signal of CO 400 ppm is read out. Then the CO concentration is determined in a similar manner. The processing in this case is similar to the processing using two standard signals of CO 65 ppm and 200 ppm. The standard signal of CO 400 ppm is used in place of the standard signal of CO 65 ppm.

Figure 11:
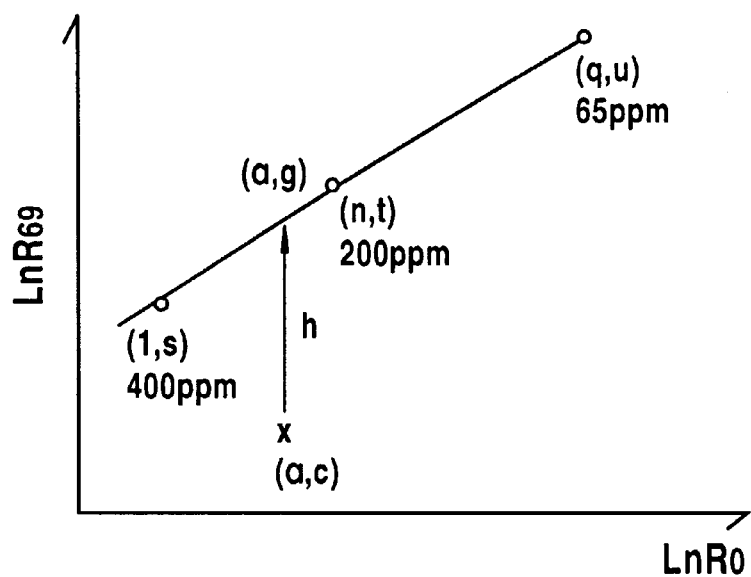
FIG. 11 is a characteristic diagram showing a mechanism for detecting coexisting hydrogen in the embodiment.
Figure 13:
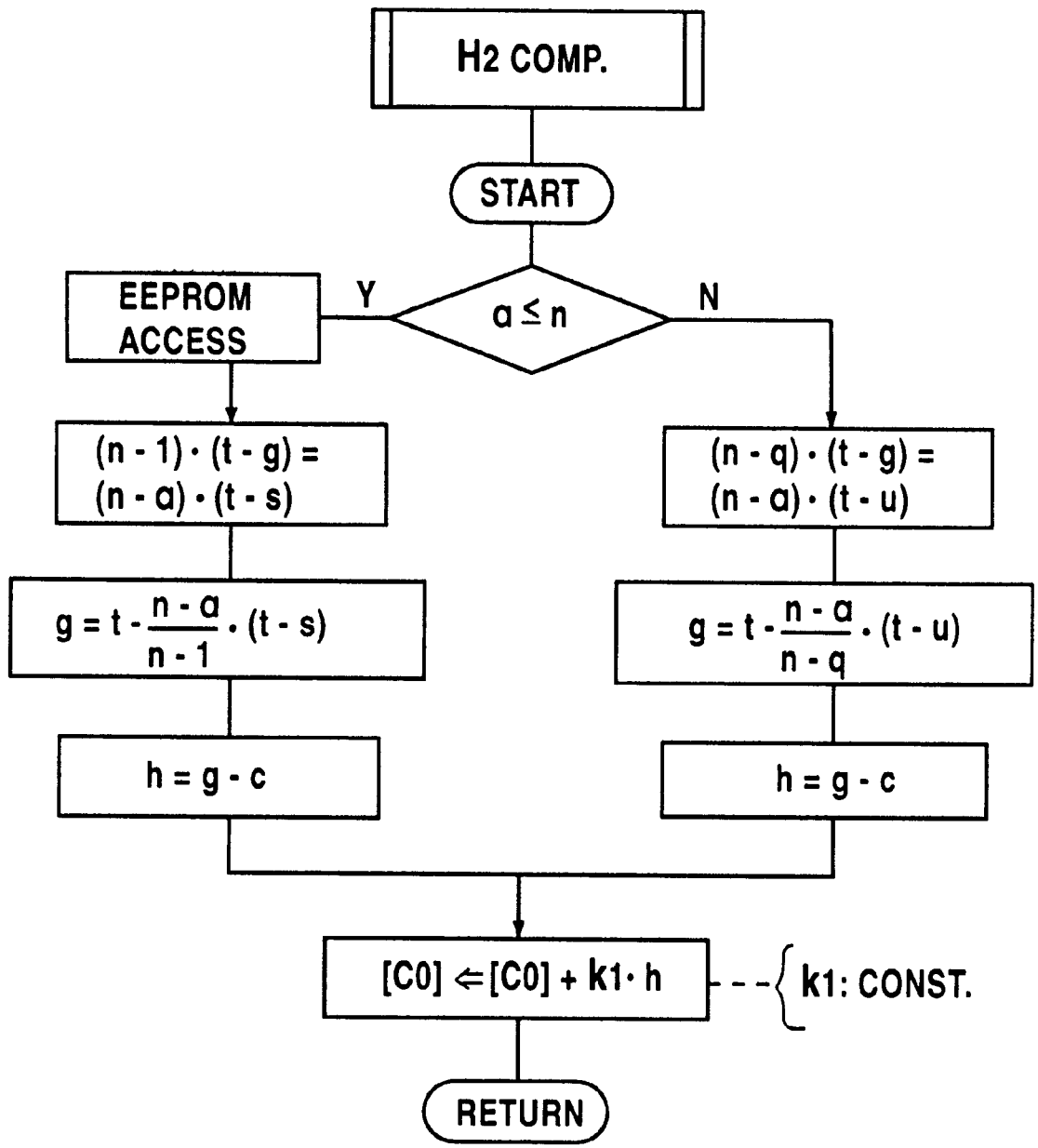
FIG. 13 is a flow chart showing compensation of coexisting hydrogen in the gas detector of the embodiment.

When the CO concentration is determined, the next step is hydrogen compensation. The procedure is shown in FIG. 13, and the principle is shown in FIG. 11. Coordinates of a measuring point are assumed to be (a,c) in a two-dimensional topological space that is determined by the logarithm of the resistance at the 0th second and the logarithm of the resistance at the 69th second. The point is vertically translated in FIG. 11 to intersect the CO concentration axis of 65 ppm, 200 ppm and 400 ppm. The coordinates of the intersection point are expressed by (a, g). The difference between g and c is h. It is assumed that the hydrogen concentration is determined by h. In this case, it is judged whether the signal of 400 ppm is needed as a standard signal by checking whether the value of a exceeds n or not. When a is n or under, the EEPROM 20 is accessed to read out the standard signal of 400 ppm. As the point (a, g) is on a segment that connects the standard signal of 200 ppm and the standard signal of 400 ppm, one expression concerning the coordinate g is generated. g can be determined from this expression. When g is determined, then h can be determined. Then k1×h is added to the CO concentration determined by the main loop of FIG. 12. k1 is an appropriate positive constant. The standard of this addition is to null the hydrogen concentration dependency of the CO detector or to set the ratio of CO sensitivity and hydrogen sensitivity at an appropriate value such as 10:1. When a is greater than n or the point (a, c) that is determined in FIG. 11 is on the right of the standard signal of 200 ppm, the standard signals of 65 ppm and 200 ppm are used. Then h is determined in a manner similar to that mentioned above to make hydrogen concentration compensation.

After hydrogen concentration compensation, the operation goes back to the main loop of FIG. 13 to determine the CO hemoglobin concentration in blood COHb from the CO concentration. The initial value of COHb is set at zero at the time of resetting. This transformation itself is well known, k2, k3, k4 are constants, and here k4 is a value corresponding to about CO 30 ppm that is below the minimum limit of detection; thus detection is not made when the CO concentration is below 30 ppm.

Figure 14:
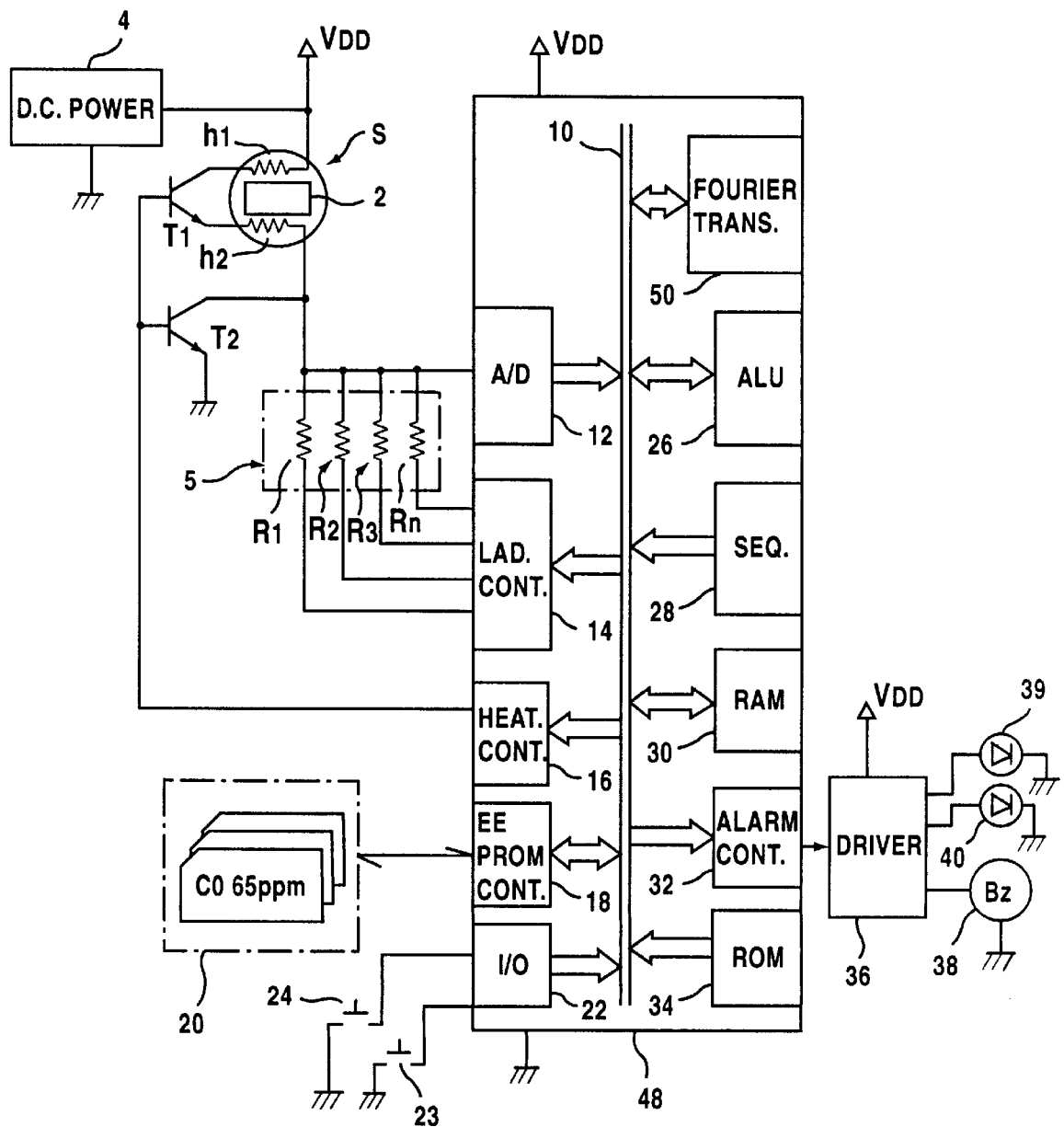
FIG. 14 is a block diagram of a gas detector of a modification.

A modification using Fourier transformation is used in FIG. 14. This modification is identical to the embodiment except a new microcomputer 48 is used and a Fourier transform sample 50 is provided. However, as Fourier transformation is used, the microcomputer 48 is, for example, of a 8-bit type. To detect CO, in the case of Fourier transformation, temperature change of a square waveform is not desirable. Hence the waveform of the sensor temperature is set as, for example, a sine waveform of a total period of 120 seconds; a higher temperature period of 60 seconds and a lower temperature period of 60 seconds. Then four components are used: Fourier transform component, or Fourier series synchronized to the temperature change in a period of 120 seconds (basic sine wave), a component that has a period of 120 seconds and is advanced by 90 degrees in phase (basic cosine wave); and harmonic components; a sine component and a cosine component, each having a period of 60 seconds. With these four components, detection similar to that of the embodiment of FIG. 1 through FIG. 13 can be done after making Fourier transformation. In other aspects, the modification of FIG. 14 is similar to the embodiment of FIG. 1 through FIG. 13. In other words, in the EEPROM 20, are stored a total of four components; sine and cosine components of 120 sec period and 60 sec period at three concentrations, 65, 200 and 400 ppm. Standard signals are a total of 12=4×3. In Fourier transformation, the sensor resistance is constantly AD-converted, or a waveform component that has a high correlation with CO from the last part of the lower temperature period to the early part of the higher temperature period and a waveform component that has a high correlation with hydrogen in the early part of the lower temperature period are AD-converted. The ladder resistance control 14 monitors, for example, the value of the output voltage V R1 every one second, and control the ladder resistance 5 so that V R1 is within the proper range after the next one second. As for Fourier transformation, logarithms of sensor resistance values at 60 points of the 120 sec period are used, and the logarithms of sensor resistance values are subjected to Fourier transformation and compared with the four standard signals.

We claim:

1. A gas detector detecting a gas by subjecting a metal oxide semiconductor gas sensor to a temperature change, a resistance of said gas sensor changing with the gas, said gas detector comprising:

a non-volatile memory means for storing a standard signal being linear to logarithms of resistance values of said metal oxide semiconductor in combination with plural points on a waveform of the resistance of the gas sensor according to the temperature change;

a ladder resistance being connected as a load resistance in series with said gas sensor, a ratio of its resistance to that of the metal oxide semiconductor being arranged to be within a specified range at said plural points;

a power source for applying a detecting voltage to said ladder resistance and said metal oxide semiconductor;

a sampling means for sampling measurement data being linear to the logarithm of the resistance value of said metal oxide semiconductor by sampling an output linear to an output voltage to said ladder resistance at each of said plural points; and a gas detecting means for detecting the gas by comparing combinations of measurement data at said plural points with said standard signal.

2. A gas detector of claim 1 characterized in that in said sampling means, said output is transformed into said measurement data by $$LnR = 2 - 4\ VR1/Vc + LnR1$$

where R indicating the resistance of the metal oxide semiconductor, V R1 the output voltage to the ladder resistance, Vc the detecting voltage, R1 the resistance of the ladder resistance, and Ln natural logarithm, respectively.

3. A gas detector of claim 1 characterized in that in said sampling means, said output is transformed into said measurement data by $$\text{Ln}R = 2x + 2x^3/3 + \text{Ln}R1 \text{ and}$$

$$x = 1 - 2\,VR1/Vc$$

where R indicating the resistance of the metal oxide semiconductor, V R1 the output voltage to the ladder resistance, Vc the detecting voltage, R1 the resistance of the ladder resistance, and Ln natural logarithm, respectively.

4. A gas detector of claim 3 characterized in that said ladder resistance is configured so that a resistance ratio of said metal oxide semiconductor and said ladder resistance is kept within a range of from 4 to ¼ at said plural points.

5. A gas detector of claim 2 characterized in that said ladder resistance is configured so that the resistance ratio of said metal oxide semiconductor and said ladder resistance is kept within a range of from 2 to ½ at said plural points.

6. A gas detector of claim 1 characterized in that for at least one point of said plural points, the resistance value of the ladder resistance is switched according to said output at the preceding point thereof.

7. A gas detector of claim 1 characterized in that said non-volatile memory is an EEPROM, and standard signals at least three gas concentrations are stored in the EEPROM, that a volatile memory is provided, and out of the standard signals stored in said EEPROM, standard signals of two lower concentrations are read out of the EEPROM into said volatile memory, and that in said gas detecting means, measurement data are compared with the standard signals stored in the volatile memory, and standard signals to be stored in the volatile memory are changed.

* * * * *